(12) United States Patent
Zheng et al.

(10) Patent No.: US 10,876,944 B1
(45) Date of Patent: Dec. 29, 2020

(54) SHEAR BOX FOR TESTING CYCLIC SHEAR CHARACTERISTICS OF A ROCK MASS DISCONTINUITY

(71) Applicant: INSTITUTE OF GEOLOGY AND GEOPHYSICS, CHINESE ACADEMY OF SCIENCES, Beijing (CN)

(72) Inventors: Bowen Zheng, Beijing (CN); Shengwen Qi, Beijing (CN); Songfeng Guo, Beijing (CN); Xiaolin Huang, Beijing (CN); Ning Liang, Beijing (CN); Yu Zou, Beijing (CN); Zhifa Zhan, Beijing (CN); Libo Jiang, Beijing (CN); Xin Wang, Beijing (CN)

(73) Assignee: INSTITUTE OF GEOLOGY AND GEOPHYSICS, CHINESE ACADEMY OF SCIENCES, Beijing (CN)

( * ) Notice: Subject to any disclaimer, the term of this patent is extended or adjusted under 35 U.S.C. 154(b) by 0 days.

(21) Appl. No.: 16/833,687

(22) Filed: Mar. 30, 2020

(30) Foreign Application Priority Data

Jul. 15, 2019 (CN) .......................... 2019 1 0633628

(51) Int. Cl.
*G01N 3/00* (2006.01)
*G01N 3/24* (2006.01)
*G01N 3/02* (2006.01)

(52) U.S. Cl.
CPC ................ *G01N 3/24* (2013.01); *G01N 3/02* (2013.01); *G01N 2203/0025* (2013.01)

(58) Field of Classification Search
CPC ..... G01N 3/24; G01N 3/02; G01N 2203/0025
USPC ........................................................... 73/841
See application file for complete search history.

(56) References Cited

U.S. PATENT DOCUMENTS

| | | | | |
|---|---|---|---|---|
| 4,557,147 | A * | 12/1985 | Rohde ...................... | G01N 3/24 73/784 |
| 5,063,785 | A * | 11/1991 | Labuz ...................... | G01N 3/10 73/821 |
| 2015/0068319 | A1* | 3/2015 | He ........................... | G01N 3/30 73/838 |
| 2018/0031457 | A1* | 2/2018 | Jiang ........................ | G01N 3/02 |
| 2018/0031458 | A1* | 2/2018 | Jiang ....................... | G01N 19/04 |

(Continued)

FOREIGN PATENT DOCUMENTS

CN 105865942 A 8/2016

*Primary Examiner* — Max H Noori
(74) *Attorney, Agent, or Firm* — Bayramoglu Law Offices LLC

(57) ABSTRACT

A shear box for testing cyclic shear characteristics of a rock mass discontinuity includes: an upper shear box including an upper semi-open cavity composed of an upper left side plate, an upper right side plate, an upper front side plate, an upper rear side plate and an upper top plate; and a lower shear box including a lower semi-open cavity composed of a lower left side plate, a lower right side plate, a lower front side plate, a lower rear side plate and a lower bottom plate; the upper shear box includes at least one first adjusting device for adjusting a space size of the upper semi-open cavity; the lower shear box includes at least one second adjusting device for adjusting a space size of the lower semi-open cavity; and the upper shear box and the lower shear box are placed opposite to each other.

14 Claims, 5 Drawing Sheets

(56) References Cited

U.S. PATENT DOCUMENTS

| 2019/0011344 | A1* | 1/2019 | Zhou | G01N 3/10 |
| 2020/0182760 | A1* | 6/2020 | Yang | G01N 3/12 |

* cited by examiner

SHEAR BOX FOR TESTING CYCLIC SHEAR CHARACTERISTICS OF A ROCK MASS DISCONTINUITY

CROSS REFERENCE TO THE RELATED APPLICATIONS

This application is based upon and claims priority to Chinese Patent Application No. 201910633628.8, filed on Jul. 15, 2019, the entire contents of which are incorporated herein by reference.

TECHNICAL FIELD

The present invention belongs to the field of laboratory tests of rock mass mechanics, and specifically provides a shear box for testing cyclic shear characteristics of a rock mass discontinuity.

BACKGROUND

Rock masses are composed of rock blocks and discontinuities, and shear strength parameters of the discontinuities are important indicators for evaluating the stability of engineering rock masses in low stress regions. With the implementation of the "One Belt One Road" strategy in China, a large number of projects will inevitably be built in the high seismic intensity regions of western China. Therefore, the seismic stability of engineering rock masses has become a focus of common concern in the engineering and scientific communities. Unlike gravity, a seismic load changes with time and is a dynamic cyclic load. For engineering rock masses that are stable under gravity conditions, the morphology of the discontinuities is degraded and the strength is weakened under dynamic cyclic shearing of the seismic load, causing the rock masses to shift or slip along the discontinuities, thus causing landslide disasters. Therefore, quantitative characterization of the shear strength characteristics of rock mass discontinuities under a seismic dynamic cyclic load is critical to seismic stability evaluation of engineering rock masses.

The cyclic shear effect of seismic loads on rock mass discontinuities was generalized by previous researchers into a cyclic shear laboratory test of the discontinuities, and the cyclic shear characteristics of natural rock mass discontinuities and artificial rock mass discontinuities were studied by laboratory direct shear tests. To obtain accurate and reliable results of cyclic shear tests on discontinuities, in the tests, it is necessary to ensure that the samples and the inner walls of the shear boxes of the test systems seamlessly and closely contact to meet the research needs of cyclic shear tests on rock mass discontinuities with different sizes. To solve this technical problem more conveniently and effectively, the present invention provides a shear box for testing cyclic shear characteristics of a rock mass discontinuity.

SUMMARY

To solve the above problems in the prior art, namely, for meeting the research needs of cyclic shear tests on rock mass discontinuities with different sizes, the present invention provides a shear box for testing cyclic shear characteristics of a rock mass discontinuity to obtain accurate and reliable results of shear tests on discontinuities, thereby providing key cyclic shear strength parameters of discontinuities for seismic stability evaluation of engineering rock masses. The shear box for testing cyclic shear characteristics of the rock mass discontinuity includes: an upper shear box including an upper semi-open cavity composed of an upper left side plate, an upper right side plate, an upper front side plate, an upper rear side plate and an upper top plate, and a lower shear box including a lower semi-open cavity composed of a lower left side plate, a lower right side plate, a lower front side plate, a lower rear side plate and a lower bottom plate. The upper shear box further includes at least one first adjusting device for adjusting a space size of the upper semi-open cavity; the lower shear box further comprises at least one second adjusting device for adjusting a space size of the lower semi-open cavity; and the upper shear box and the lower shear box can be placed opposite to each other, allowing the upper semi-open cavity and the lower semi-open cavity to form an accommodating cavity for placing a rock mass to be tested.

In a preferred embodiment of the shear box for testing the cyclic shear characteristics of the rock mass discontinuity described above, the first adjusting device includes an upper isosceles trapezoid and a lower isosceles trapezoid that are oppositely arranged and connected to each other, and a left isosceles trapezoid and a right isosceles trapezoid that are oppositely arranged and connected to each other; two waist surfaces of the upper isosceles trapezoid are in contact with an upper waist surface of the left isosceles trapezoid and an upper waist surface of the right isosceles trapezoid, respectively; two waist surfaces of the lower isosceles trapezoid are in contact with a lower waist surface of the left isosceles trapezoid and a lower waist surface of the right isosceles trapezoid, respectively; and the first adjusting device adjusts the space size of the upper semi-open cavity by adjusting a relative position of the upper isosceles trapezoid and the lower isosceles trapezoid and a relative position of the left isosceles trapezoid and the right isosceles trapezoid.

In a preferred embodiment of the shear box for testing the cyclic shear characteristics of the rock mass discontinuity described above, the upper isosceles trapezoid and the lower isosceles trapezoid are connected to each other by bolts; and/or the left isosceles trapezoid and the right isosceles trapezoid are connected to each other by pins.

In a preferred embodiment of the shear box for testing the cyclic shear characteristics of the rock mass discontinuity described above, two first adjusting devices are provided on left and right sides of the upper shear box, respectively; wherein the left isosceles trapezoid of the first adjusting device on the left side is connected to an inner side of the upper left side plate, and the right isosceles trapezoid of the first adjusting device on the right side is connected to an inner side of the upper right side plate.

In a preferred embodiment of the shear box for testing the cyclic shear characteristics of the rock mass discontinuity described above, the upper shear box further includes two first pads; wherein one of the two first pads is connected to the right isosceles trapezoid of the first adjusting device on the left side, and the other of the two first pads is connected to the left isosceles trapezoid of the first adjusting device on the right side.

In a preferred embodiment of the shear box for testing the cyclic shear characteristics of the rock mass discontinuity described above, the upper shear box has the same structure as the lower shear box; and/or the second adjusting device has the same structure as the first adjusting device.

In a preferred embodiment of the shear box for testing the cyclic shear characteristics of the rock mass discontinuity described above, two second adjusting devices are arranged on left and right sides of the lower shear box, respectively; wherein the left isosceles trapezoid of the second adjusting device on the left side is connected to an inner side of the lower left side plate, and the right isosceles trapezoid of the second adjusting device on the right side is connected to an inner side of the lower right side plate.

In a preferred embodiment of the shear box for testing the cyclic shear characteristics of the rock mass discontinuity described above, the lower shear box further includes two second pads; wherein one of the two second pads is connected to the right isosceles trapezoid of the second adjusting device on the left side, and the other of the two second pads is connected to the left isosceles trapezoid of the second adjusting device on the right side.

In a preferred embodiment of the shear box for testing the cyclic shear characteristics of the rock mass discontinuity described above, lower end surfaces of the first pads are flush with lower end surfaces of the left isosceles trapezoid and the right isosceles trapezoid in the first adjusting device, respectively; upper end surfaces of the second pads are flush with upper end surfaces of the left isosceles trapezoid and the right isosceles trapezoid in the second adjusting device, respectively; and/or, upper end surfaces of the upper left side plate and the upper right side plate in the upper shear box are separately flush with an upper end surface of the upper top plate; lower end surfaces of the upper left side plate and the upper right side plate in the upper shear box are flush with lower end surfaces of the upper front side plate and the upper rear side plate, respectively; lower end surfaces of the lower left side plate and the lower right side plate in the lower shear box are separately flush with a lower end surface of the lower bottom plate; and upper end surfaces of the lower left side plate and the lower right side plate in the lower shear box are flush with upper end surfaces of the lower front side plate and the lower rear side plate, respectively.

In a preferred embodiment of the shear box for testing the cyclic shear characteristics of the rock mass discontinuity described above, the lower end surfaces of the upper front side plate and the upper rear side plate are provided to be a structure having a first groove in the middle, respectively; the upper end surfaces of the lower front side plate and the lower rear side plate are provided to be a structure having a second groove in the middle, respectively; and in a case where the upper shear box is placed opposite to the lower shear box, the first groove is placed opposite to the second groove, so that the rock mass to be tested placed in the accommodating cavity can be observed from the outside.

The present invention adjusts the width of the first adjusting device and the second adjusting device in the upper shear box and the lower shear box and then changes the positions between the two first pads and between the two second pads to slightly adjust the space sizes of the semi-open cavities in the upper shear box and the lower shear box, or may also disassemble the first pad and the second pad in the upper shear box and the lower shear box (that is, the first pad and the second pad are removed or the first pad and the second pad are not installed) to greatly adjust the space sizes of the semi-open cavities, to eliminate the gaps formed between the rock masses to be tested with different sizes and the shear box, where the gaps are perpendicular to a length direction of the shear box, thus ensuring the reliability of the cyclic shear test results of the rock mass discontinuity. Therefore, the purpose of the experimental research on cyclic shear characteristics of the rock mass discontinuity is achieved. Moreover, the shear box provided by the present invention can conveniently and efficiently meet the research needs of cyclic shear tests on rock mass discontinuities with different sizes by a structural design and adjustment method combining a macro adjustment and a fine adjustment, thereby providing key cyclic shear strength parameters of discontinuities for seismic stability evaluation of engineering rock masses.

Figure 1:
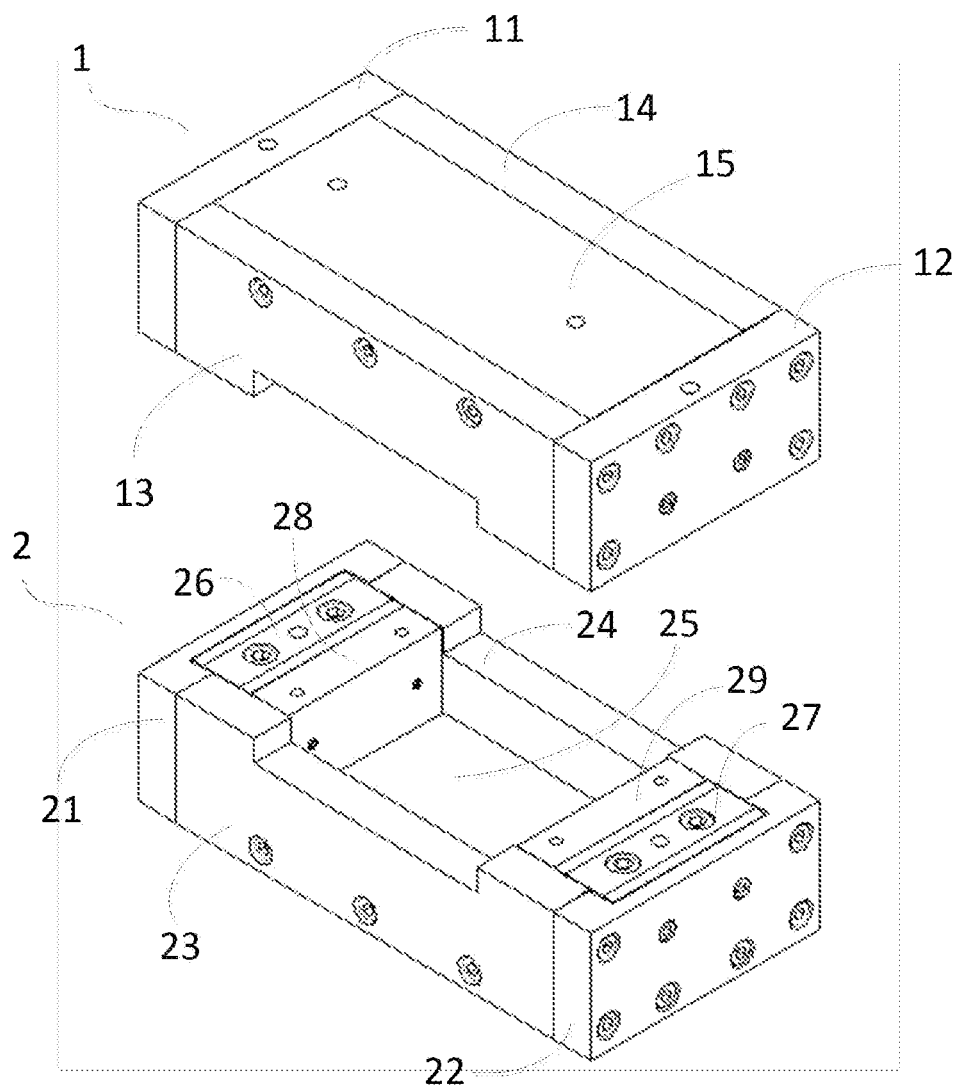
FIG. 1 is a schematic view of the overall structure of a shear box for testing cyclic shear characteristics of a rock mass discontinuity according to the present invention.

Reference numerals in the figures are described below:

1—upper shear box, 11—upper left side plate, 12—upper right side plate, 13—upper front side plate, 14—upper rear side plate, 15—upper top plate; 2—lower shear box, 21—lower left side plate, 22—lower right side plate, 23—lower front side plate, 24—lower rear side plate, 25—lower bottom plate; 26—left second adjusting device, 261—upper isosceles trapezoid, 262—lower isosceles trapezoid, 263—left isosceles trapezoid, 264—right isosceles trapezoid; 27—right second adjusting device; 28—left second pad, 29—right second pad; M—bolt hole, N—pin hole, and T—avoiding hole.

DETAILED DESCRIPTION OF THE EMBODIMENTS

To make the embodiments, technical solutions, and advantages of the present invention more obvious, the technical solutions of the present invention are clearly and completely described below with reference to the accompanying drawings. It is obvious that the described embodiments are a part of the embodiments of the present invention, but not all embodiments. It should be understood by those skilled in the art that these embodiments are only used to explain the technical principles of the present invention, and are not intended to limit the protection scope of the present invention. In addition, the orientations mentioned in the present embodiment, such as up, down, left, right, front, back, inside, and outside, are the orientations of the shear box of the present invention in the actual use, and are also the orientations in the accompanying drawings.

First of all, referring to FIG. 1, FIG. 1 is a schematic view of the overall structure of a shear box for testing cyclic shear characteristics of a rock mass discontinuity according to the present invention. As shown in FIG. 1, the shear box of the present invention includes the upper shear box 1 and the lower shear box 2. The upper shear box 1 includes an upper semi-open cavity composed of the upper left side plate 11, the upper right side plate 12, the upper front side plate 13, the upper rear side plate 14, and the upper top plate 15; and the lower shear box 2 includes a lower semi-open cavity composed of the lower left side plate 21, the lower right side plate 22, the lower front side plate 23, the lower rear side plate 24, and the lower bottom plate 25.

In a specific embodiment, the upper shear box 1 and the lower shear box 2 may be designed to have the same structure, and the upper shear box 1 is equivalent to the lower shear box 2 upside down. In this way, after the upper shear box 1 and the lower shear box 2 are oppositely placed, the two semi-open cavities (i.e. the upper semi-open cavity of the upper shear box and the lower semi-open cavity of the lower shear box) are oppositely placed, so that the upper semi-open cavity and the lower semi-open cavity form an accommodating cavity for placing a rock mass to be tested. Since the upper shear box 1 has the same structure as the lower shear box 2, for convenience of description, the structure of the lower shear box 2 is described below as an example.

Continuing to refer to FIG. 1, as a specific embodiment, the lower front side plate 23 and the lower rear side plate 24 are connected and fixed to the front and rear sides of the lower bottom plate 25 by bolt devices, respectively. The lower left side plate 21 and the lower right side plate 22 are connected and fixed to left and right sides of the lower front side plate 23, the lower rear side plate 24 and the lower bottom plate 25 by bolt devices, respectively. The lower shear box 2 forms one semi-open rectangular box structure.

More specifically, the lower shear box 2 further includes at least one second adjusting device for adjusting a space size of the lower semi-open cavity. Continuing to refer to FIG. 1, in this embodiment, the lower shear box 2 includes two second adjusting devices, namely, the left second adjusting device 26 on the left side and the right second adjusting device 27 on the right side as shown in FIG. 1. The upper shear box 1 further includes at least one first adjusting device for adjusting a space size of the upper semi-open cavity. As an example, the first adjusting device and the second adjusting device may be designed to have the same structure. Although the first adjusting devices are not shown in the upper shear box 1 in FIG. 1, in this embodiment, the upper shear box 1 also includes two first adjusting devices, namely, a left first adjusting device on the left side and a right first adjusting device on the right side.

Since the first adjusting device has the same structure as the second adjusting device, the structure of the second adjusting device is described below with reference to FIGS. 2a-2g. Because the left second adjusting device 26 has the same structure as the right second adjusting device 27, the left second adjusting device 26 is described below as an example.

Figure 2A:
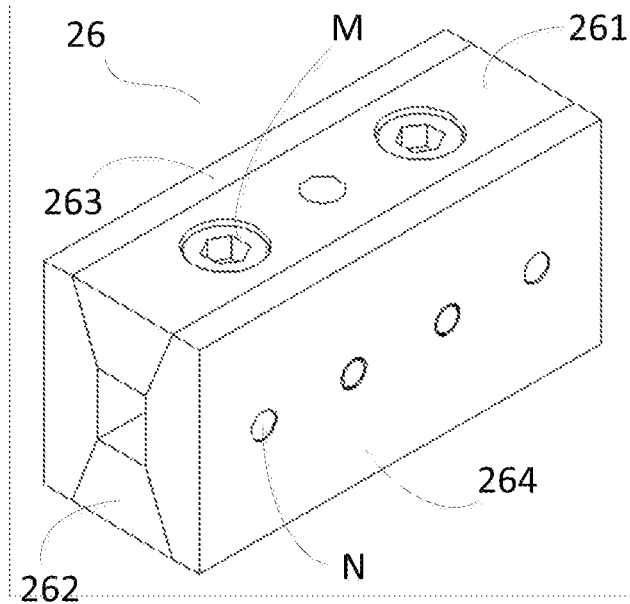
FIG. 2a is a structural schematic view of a left second adjusting device of a lower shear box of the present invention.
Figure 2B:
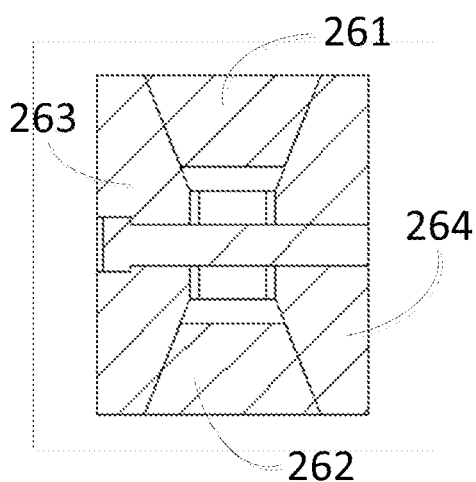
FIG. 2b is a schematic cross-sectional view of the overall structure of the left second adjusting device of the present invention.
Figure 2C:
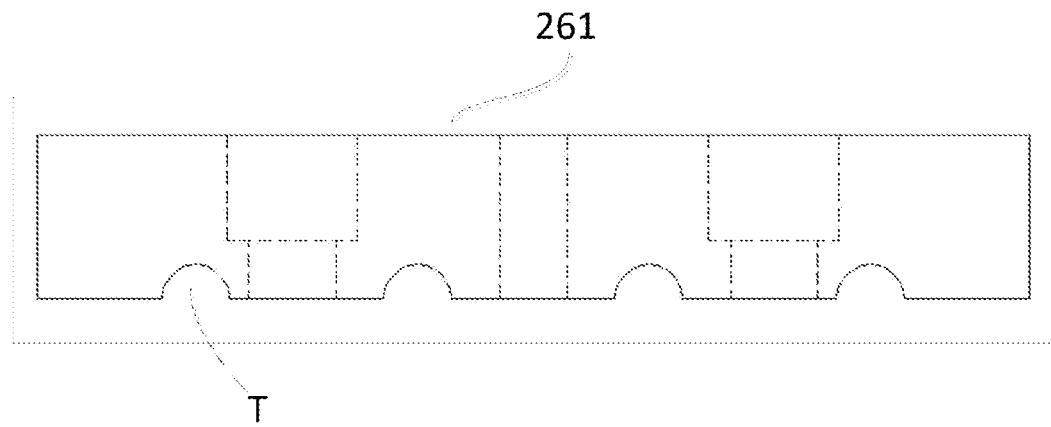
FIG. 2c is a front view of an upper isosceles trapezoid of the left second adjusting device of the present invention.
Figure 2D:
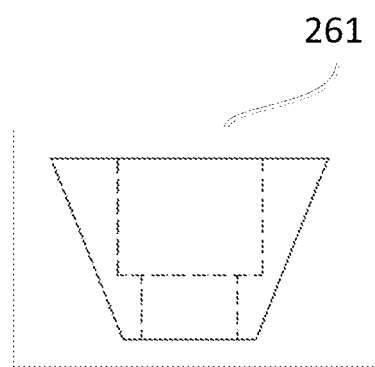
FIG. 2d is a side view of the upper isosceles trapezoid of the left second adjusting device of the present invention.
Figure 2E:
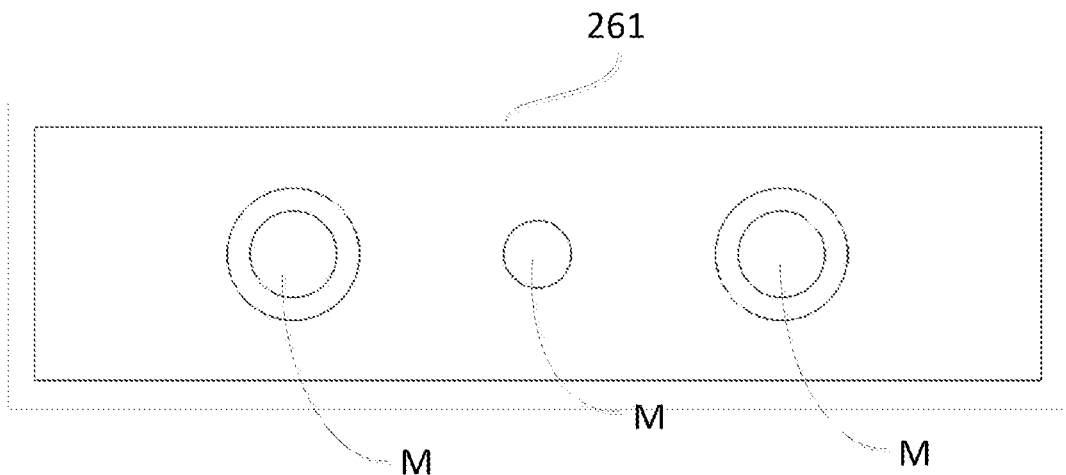
FIG. 2e is a top view of an upper isosceles trapezoid of the left second adjusting device of the present invention.
Figure 2F:
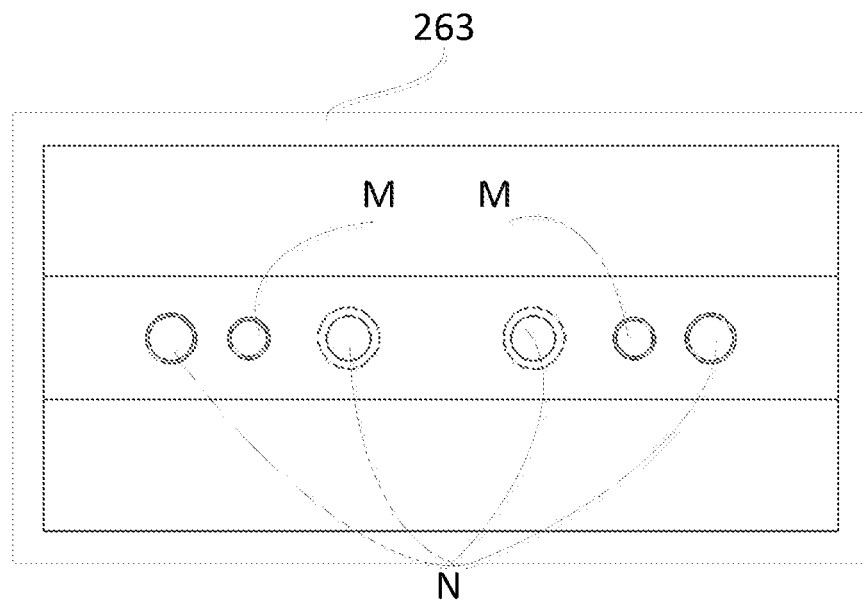
FIG. 2f is a front view of a left isosceles trapezoid of the left second adjusting device of the present invention.
Figure 2G:
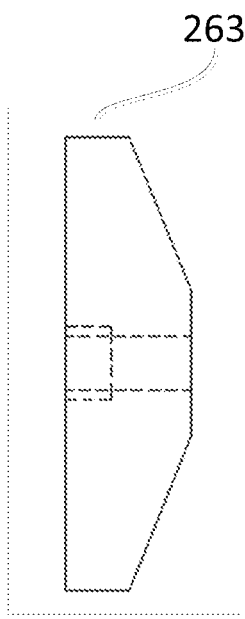
FIG. 2g is a side view of the left isosceles trapezoid of the left second adjusting device of the present invention.

FIGS. 2a and 2b are a schematic structural view and a cross-sectional view of the left second adjusting device 26 of the lower shear box 2 in the present invention, respectively. As shown in FIGS. 2a and 2b, the left second adjusting device 26 includes the upper isosceles trapezoid 261 and the lower isosceles trapezoid 262 that are oppositely provided and connected to each other, and further includes the left isosceles trapezoid 263 and the right isosceles trapezoid 264 that are oppositely disposed and connected to each other. Among them, two waist surfaces of the upper isosceles trapezoid 261 are in contact with an upper waist surface of the left isosceles trapezoid 263 and an upper waist surface of the right isosceles trapezoid 264, respectively; and two waist surfaces of the lower isosceles trapezoid 262 are in contact with a lower waist surface of the left isosceles trapezoid 263 and a lower waist surface of the right isosceles trapezoid 264, respectively. In other words, the trapezoidal surface having a smaller area in the upper isosceles trapezoid 261 is provided opposite to that in the lower isosceles trapezoid 262; and the trapezoidal surface having a smaller area in the left isosceles trapezoid 263 is provided opposite to that in the right isosceles trapezoid 264. In this embodiment, as shown in FIG. 2b, the upper isosceles trapezoid 261 has the same cross-sectional area as the lower isosceles trapezoid 262, and the left isosceles trapezoid 263 has the same cross-sectional area as the right isosceles trapezoid 264. In this way, the second adjusting device may be used to adjust the space size of the lower semi-open cavity by adjusting a relative position of the upper isosceles trapezoid 261 and the lower isosceles trapezoid 262 and a relative position of the left isosceles trapezoid 263 and the right isosceles trapezoid 264.

In more detail, referring to FIGS. 2c-2g, FIGS. 2c-2g are respectively a front view of the upper isosceles trapezoid 261 of the left second adjusting device 26, a side view of the upper isosceles trapezoid 261, a top view of the upper isosceles trapezoid 261, a front view of the left isosceles trapezoid 263, and a side view of the left isosceles trapezoid 263 in the present invention. As shown in FIGS. 2c-2g, the outer surface of the upper isosceles trapezoid 261 is provided with the bolt holes M (those skilled in the art can set appropriate bolt holes M according to actual needs), the inner surface of the upper isosceles trapezoid 261 is provided with the avoiding holes T. The outer surface of the left isosceles trapezoid 263 is provided with the bolt holes M (the bolt holes M can be used to connect to the lower left side plate 21) and the pin holes N (those skilled in the art can set appropriate bolt holes M and pin holes N according to actual needs). In this embodiment, the upper isosceles trapezoid 261 and the lower isosceles trapezoid 262 have the same structure and are symmetrically provided. The left isosceles trapezoid 263 and the right isosceles trapezoid 264 have the same structure and are symmetrically provided. A method for assembling the second adjusting device is as follows: the upper isosceles trapezoid 261 is connected to the lower isosceles trapezoid 262 by a bolt device. Specifically, two bolts may be inserted from the bolt holes M on the outer surface of the upper isosceles trapezoid 261 and penetrate into the inner surface of the lower isosceles trapezoid 262, respectively. The left isosceles trapezoid 263 is connected to the right isosceles trapezoid 264 by a pin device. Specifically, two pins may be inserted from the pin holes N on the outer surface of the left isosceles trapezoid 263 and penetrate into the inner surface of the right isosceles trapezoid 264 without penetrating the right isosceles trapezoid 264, respectively. Since the inner surfaces of the upper isosceles trapezoid 261 and the lower isosceles trapezoid 262 are provided with the avoiding holes T, the pins can pass through the avoiding holes T.

The above-mentioned "the upper isosceles trapezoid 261 and the lower isosceles trapezoid 262 have the same structure and are symmetrically provided, and the left isosceles trapezoid 263 and the right isosceles trapezoid 264 have the same structure and are symmetrically provided" needs to be further described herein. Due to assembly needs, for example, when the upper isosceles trapezoid 261 is connected to the lower isosceles trapezoid 262 by the bolt device, the bolt holes on the upper isosceles trapezoid 261 is slightly different from that on the lower isosceles trapezoid 262 in general (the upper isosceles trapezoid 261 corresponds to a bolt head, and the lower isosceles trapezoid 262 corresponds to a bolt tail). Even if such a difference exists due to the assembly needs, the upper isosceles trapezoids 261 can be considered to have the same structure as the lower isosceles trapezoid 262. For the same reason, the left isosceles trapezoid 263 and the right isosceles trapezoid 264 may also be provided with different pin holes according to the actual assembly needs. These assembly differences can be flexibly designed by those skilled in the art according to the actual assembly needs. Even if such a difference exists due to the assembly needs, the left isosceles trapezoid 263 can be considered to have the same structure as the right isosceles trapezoid 264.

Referring back to FIG. 1, taking the method for assembling the left second adjusting device 26 as an example, the left second adjusting device 26 is connected to the lower left side plate 21 by a bolt device. Specifically, the outer surface of the left isosceles trapezoid 263 of the left second adjusting device 26 is fixed to the inner surface of the lower left side plate 21 by bolts.

Further, the upper shear box 1 of the present invention further includes two first pads, and the lower shear box 2 includes two second pads. The upper shear box 1 has the same structure as the lower shear box 2, and the structures of the first pad and the second pad may also be set to have the same structure. The lower shear box 2 is taken as an example to describe the specific structure of the second pad.

As shown in FIG. 1, the lower shear box 2 includes two second pads, namely, the left second pad 28 on the left side and the right second pad 29 on the right side. The left second pad 28 is connected to the left second adjusting device 26 through a pin device along its width direction, and the right second pad 29 is connected to the right second adjusting device 27 through a pin device along its width direction. A more specific connection method may be as follows: the left second pad 28 and the right second pad 29 are provided with pin holes distributed horizontally parallel to each other and penetrating back and forth along their width directions, respectively, and the positions of the pin holes can correspond to the pin holes provided on the right isosceles trapezoid of the left second adjusting device 26 and the left isosceles trapezoid of the right second adjusting device 27, respectively. In this way, pins can pass through the pin holes of the left second pad 28 (the right second pad 29) and the right isosceles trapezoid of the left second adjusting device 26 (the left isosceles trapezoid of the right second adjusting device 27). As an example, after a pin passes through the left second pad 28 and the right isosceles trapezoid of the left second adjusting device 26, it can also penetrate into (but not penetrate through) the left isosceles trapezoid of the left second adjusting device 26; and after a pin passes through the right second pad 29 and the left isosceles trapezoid of the right second adjusting device 27, it can also penetrate into (but not penetrate through) the right isosceles trapezoid of the right second adjusting device 27. Preferably, the left second pad 28 (the right second pad 29) is further provided with a pin hole along its height direction, and the position of the pin hole intersects with but does not pass through the pin hole passing through the left second pad 28 (the right second pad 29) along its width direction.

Figure 3A:
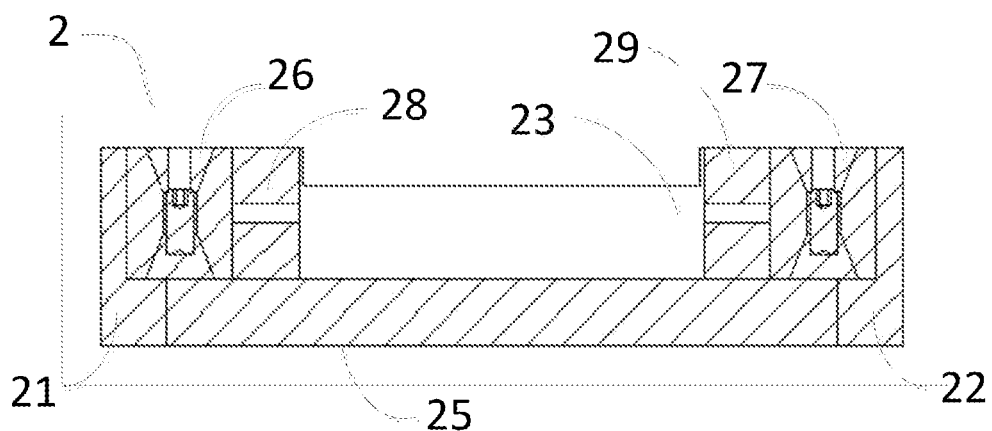
FIG. 3a is a front view of a lower shear box of the present invention.
Figure 3B:
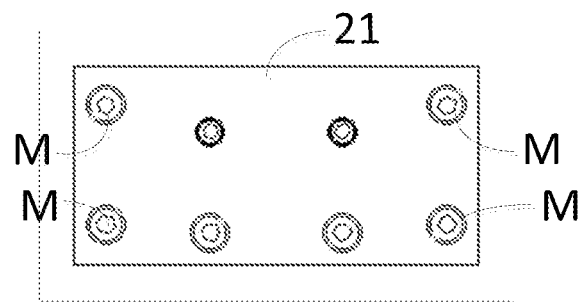
FIG. 3b is a left side view of the lower shear box of the present invention.
Figure 3C:
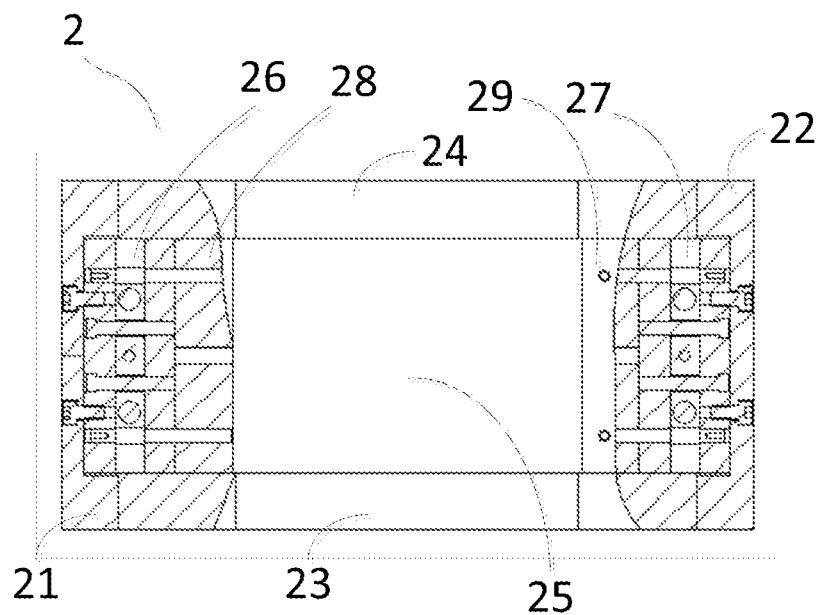
FIG. 3c is a top view of the lower shear box of the present invention.

To more clearly understand the structure of each part of the lower shear box 2 of the present invention and the connection relationship thereof, reference is made to FIGS. 3a, 3b, and 3c below. FIGS. 3a, 3b, and 3c are a front view, a left view, and a top view of the lower shear box of the present invention, respectively. It should be noted that, in this embodiment, the front view and the rear view of the lower shear box are the same, and the left view and the right view are the same. The connection relationships among the lower left side plate 21, the left second adjusting device 26, and the left second pad 28, and the connection relationships among the lower right side plate 22, the right second adjusting device 27, and the right second pad 29 are shown in FIGS. 3a, 3b, and 3c.

In a specific embodiment, as shown in FIG. 1, upper end surfaces of the two second pads are flush with upper end surfaces of the left isosceles trapezoid and the right isosceles trapezoid of the second adjusting device, respectively; and similarly, lower end surfaces of the two first pads are flush with lower end surfaces of the left isosceles trapezoid and the right isosceles trapezoid of the first adjusting device, respectively. Lower end surfaces of the lower left side plate 21 and the lower right side plate 22 in the lower shear box 2 are flush with a lower end surface of the lower bottom plate 25, respectively; and upper end surfaces of the lower left side plate 21 and the lower right side plate 22 in the lower shear box 2 are flush with upper end surfaces of the lower front side plate 23 and the lower rear side plate 24, respectively. Similarly, upper end surfaces of the upper left side plate 11 and the upper right side plate 12 in the upper shear box 1 are flush with an upper end surface of the upper top plate 15, respectively; and lower end surfaces of the upper left side plate 11 and the upper right side plate 12 in the upper shear box 1 are flush with lower end surfaces of the upper front side plate 13 and the upper rear side plate 14, respectively.

Preferably, as shown in FIG. 1, the lower end surfaces of the upper front side plate 13 and the upper rear side plate 14 are provided to be a structure having a first groove in the middle, respectively; the upper end surfaces of the lower front side plate 23 and the lower rear side plate 24 are provided to be a structure having a second groove in the middle, respectively; and in the case where the upper shear box 1 is placed opposite to the lower shear box 2, the first groove is placed opposite to the second groove so that the rock mass to be tested placed in the accommodating cavity can be seen from the outside, which makes it easy to observe the test process of the rock mass to be tested.

For the shear box structure for testing the cyclic shear characteristics of the rock mass discontinuity according to the present invention, before placing the rock mass to be tested, the space sizes of the semi-open cavities of the upper shear box 1 and the lower shear box 2 are adjusted to be slightly larger than the size of the rock mass to be tested, respectively, so that the rock mass to be tested can be placed in the accommodating cavity formed by the upper shear box 1 and the lower shear box 2. Specifically, it is realized by the first adjusting device and the second adjusting device. Taking the adjustment of the left second adjusting device 26 as an example, the following steps are included: first of all, a middle bolt of the upper isosceles trapezoid 261 of the left second adjusting device 26 is loosened, and then front and rear bolts of the upper isosceles trapezoid 261 are loosened; the relative position distance between the upper isosceles trapezoid 261 and the lower isosceles trapezoid 262 is increased, thereby reducing the relative position distance between the left isosceles trapezoid 263 and the right isosceles trapezoid 264 and causing the left isosceles trapezoid 263 and right isosceles trapezoid 264 to be in close contact with the upper isosceles trapezoid 261 and lower isosceles trapezoid 262, respectively, thus increasing the relative position distance between the left second pad 28 and the right second pad 29, causing the left second pad 28 to be in close contact with the right isosceles trapezoid 264, and finally achieving the purpose of increasing the cavity sizes of the semi-open cavities of the lower shear box 2. Similarly, each of the first adjusting device and the second adjusting device may be adjusted separately to achieve the purpose of adjusting the size of the accommodating cavity. It should be noted that the accommodating space of the accommodating cavity can also be changed in a wide range by removing the first pad and the second pad provided on the upper shear box 1 and the lower shear box 2.

Further, after the rock mass to be tested is placed in the accommodating cavity, the first adjusting device and the second adjusting device are adjusted again to reduce the space size of the accommodating cavity to a state that the first pad, the second pad, and the rock mass to be tested are in close contact. Also, taking the adjustment of the left second adjusting device 26 as an example, its steps are as follows: first of all, the front and rear bolts of the upper isosceles trapezoid 261 of the left second adjusting device 26 are tightened to reduce the relative position distance between the upper isosceles trapezoid 261 and the lower isosceles trapezoid 262; the upper isosceles trapezoid 261 and the lower isosceles trapezoid 262 are caused to push the left isosceles trapezoid 263 and the right isosceles trapezoid 264, so that the relative position distance between the left isosceles trapezoid 263 and the right isosceles trapezoid 264 is increased; and the right isosceles trapezoid 264 is caused to push the left second pad 28, so that the relative position distance between the left second pad 28 and the right second pad 29 is reduced. When the relative position distance between the left second pad 28 and the right second pad 29 is reduced to a state that the right side surface of the left second pad 28 and the left side surface of the right second pad 29 are in seamless contact with the rock mass to be tested, the middle bolt of the upper isosceles trapezoid 261 of the left second adjusting device 26 is tightened, and the front and rear pins of the left second pad 28 along its height direction are simultaneously tightened, thereby fixing the current width of the left second adjusting device 26 and the current position between the left second pad 28 and the right second pad 29 and finally achieving the purpose of the close contact between the rock mass to be tested and the accommodating cavity. Similarly, each of the first adjusting device and the second adjusting device may be adjusted separately to achieve the purpose of adjusting the size of the accommodating cavity.

Further, after the end of the test, the front and rear pins of the first pad and the second pad along their height directions, and the middle bolts and the front and rear bolts in the lower isosceles trapezoid of the first adjustment device and the upper isosceles trapezoid of the second adjustment device may be loosened successively, to increase the space sizes of the semi-open cavities of the upper shear box 1 and the lower shear box 2 for facilitating the removal of the rock mass to be tested.

As described above, the present invention adjusts the width of the first adjusting device and the second adjusting device in the upper shear box and the lower shear box and then changes the positions between the two first pads and between the two second pads to slightly adjust the space sizes of the semi-open cavities in the upper shear box and the lower shear box, or may also disassemble the first pad and the second pad in the upper shear box and the lower shear box to greatly adjust the space sizes of the semi-open cavities, to eliminate the gaps formed between the rock masses to be tested with different sizes and the shear box, where the gaps are perpendicular to a length direction of the shear box, thus ensuring the reliability of the cyclic shear test results of the rock mass discontinuity. Therefore, the purpose of the experimental research on cyclic shear characteristics of the rock mass structural surface is achieved. Moreover, the shear box provided by the present invention can conveniently and efficiently meet the research needs of cyclic shear tests on rock mass structural surfaces with different sizes by a structural design and adjustment method combining a macro adjustment and a fine adjustment, thereby providing key structural surface cyclic shear strength parameters for seismic stability evaluation of engineering rock masses.

With this, the technical solutions of the present invention have been described with reference to the preferred implementations shown in the accompanying drawings, but it is easily understood by those skilled in the art that the protection scope of the present invention is obviously not limited to these specific implementations. Without departing from the principle of the present invention, those skilled in the art can make equivalent changes or replacements to related technical features, and the technical solutions obtained by these changes or replacements shall all fall into the protection scope of the present invention.

What is claimed is:

1. A shear box for testing cyclic shear characteristics of a rock mass discontinuity, comprising:
   an upper shear box, wherein the upper shear box comprises an upper semi-open cavity composed of an upper left side plate, an upper right side plate, an upper front side plate, an upper rear side plate, and an upper top plate; and
   a lower shear box, wherein the lower shear box comprises a lower semi-open cavity composed of a lower left side plate, a lower right side plate, a lower front side plate, a lower rear side plate and a lower bottom plate;
   wherein, the upper shear box further comprises at least one first adjusting device for adjusting a space size of the upper semi-open cavity; the lower shear box further comprises at least one second adjusting device for adjusting a space size of the lower semi-open cavity; the upper shear box and the lower shear box are placed opposite to each other, the upper semi-open cavity and the lower semi-open cavity form an accommodating cavity for placing a rock mass to be tested; the at least one first adjusting device comprises a first upper isosceles trapezoid, a first lower isosceles trapezoid, a first left isosceles trapezoid, and a first right isosceles trapezoid, wherein the first upper isosceles trapezoid and the first lower isosceles trapezoid are oppositely arranged and connected to each other, and the first left isosceles trapezoid and the first right isosceles trapezoid are oppositely arranged and connected to each other; two waist surfaces of the first upper isosceles trapezoid are in contact with an upper waist surface of the first left isosceles trapezoid and an upper waist surface of the first right isosceles trapezoid, respectively; two waist surfaces of the first lower isosceles trapezoid are in contact with a lower waist surface of the first left isosceles trapezoid and a lower waist surface of the first right isosceles trapezoid, respectively; and the at least one first adjusting device adjusts the space size of the upper semi-open cavity by adjusting a relative position of the first upper isosceles trapezoid and the first lower isosceles trapezoid and a relative position of the first left isosceles trapezoid and the first right isosceles trapezoid; wherein the first upper isosceles trapezoid and the first lower isosceles trapezoid are connected to each other by bolts; and the first left isosceles trapezoid and the first right isosceles trapezoid are connected to each other by pins.

2. The shear box for testing the cyclic shear characteristics of the rock mass discontinuity according to claim 1, wherein two first adjusting devices are provided on left and right sides of the upper shear box, respectively; wherein the left isosceles trapezoid of each first adjusting device of the two first adjusting devices on the left side is connected to an inner side of the upper left side plate, and the right isosceles trapezoid of each first adjusting device of the two first adjusting devices on the right side is connected to an inner side of the upper right side plate.

3. The shear box for testing the cyclic shear characteristics of the rock mass discontinuity according to claim 2, wherein the upper shear box further comprises two first pads; wherein one of the two first pads is connected to the right isosceles trapezoid of the each first adjusting device on the left side, and the other one of the two first pads is connected to the left isosceles trapezoid of the each first adjusting device on the right side.

4. The shear box for testing the cyclic shear characteristics of the rock mass discontinuity according to claim 3, wherein the at least one second adjusting device comprises a second upper isosceles trapezoid, a second lower isosceles trapezoid, a second left isosceles trapezoid, and a second right isosceles trapezoid, wherein the second upper isosceles trapezoid and the second lower isosceles trapezoid are oppositely arranged and connected to each other, and the second left isosceles trapezoid and the second right isosceles trapezoid are oppositely arranged and connected to each other; two waist surfaces of the second upper isosceles trapezoid are in contact with an upper waist surface of the second left isosceles trapezoid and an upper waist surface of the second right isosceles trapezoid, respectively; two waist surfaces of the second lower isosceles trapezoid are in contact with a lower waist surface of the second left isosceles trapezoid and a lower waist surface of the second right isosceles trapezoid, respectively; and the second adjusting device adjusts the space size of the lower semi-open cavity by adjusting a relative position of the second upper isosceles trapezoid and the second lower isosceles trapezoid and a relative position of the second left isosceles trapezoid and the second right isosceles trapezoid; the second upper isosceles trapezoid and the second lower isosceles trapezoid are connected to each other by bolts; and the second left isosceles trapezoid and the second right isosceles trapezoid are connected to each other by pins.

5. The shear box for testing the cyclic shear characteristics of the rock mass discontinuity according to claim 4, wherein two second adjusting devices are arranged on left and right sides of the lower shear box, respectively; wherein the second left isosceles trapezoid of each second adjusting device of the two second adjusting devices on the left side is connected to an inner side of the lower left side plate, and the second right isosceles trapezoid of each second adjusting device of the two second adjusting devices on the right side is connected to an inner side of the lower right side plate.

6. The shear box for testing the cyclic shear characteristics of the rock mass discontinuity according to claim 5, wherein the lower shear box further comprises two second pads; wherein one of the two second pads is connected to the second right isosceles trapezoid of the each second adjusting device on the left side, and the other one of the two second pads is connected to the second left isosceles trapezoid of the each second adjusting device on the right side.

7. The shear box for testing the cyclic shear characteristics of the rock mass discontinuity according to claim 6, wherein lower end surfaces of the first pads are flush with lower end surfaces of the first left isosceles trapezoid and the first right isosceles trapezoid, respectively; upper end surfaces of the second pads are flush with upper end surfaces of the second left isosceles trapezoid and the second right isosceles trapezoid, respectively; and/or, upper end surfaces of the upper left side plate and the upper right side plate in the upper shear box are separately flush with an upper end surface of the upper top plate; lower end surfaces of the upper left side plate and the upper right side plate in the upper shear box are flush with lower end surfaces of the upper front side plate and the upper rear side plate, respectively; lower end surfaces of the lower left side plate and the lower right side plate in the lower shear box are separately flush with a lower end surface of the lower bottom plate; and upper end surfaces of the lower left side plate and the lower right side plate in the lower shear box are flush with upper end surfaces of the lower front side plate and the lower rear side plate, respectively.

8. The shear box for testing the cyclic shear characteristics of the rock mass discontinuity according to claim 1, wherein lower end surfaces of the upper front side plate and the upper rear side plate are provided to be a first structure having a first groove in the middle of the first structure, respectively; upper end surfaces of the lower front side plate and the lower rear side plate are provided to be a second structure having a second groove in the middle of the second structure, respectively; and when the upper shear box is placed opposite to the lower shear box, the first groove is placed opposite to the second groove, and the rock mass to be tested placed in the accommodating cavity is observed from outside.

9. The shear box for testing the cyclic shear characteristics of the rock mass discontinuity according to claim 2, wherein lower end surfaces of the upper front side plate and the upper rear side plate are provided to be a first structure having a first groove in the middle of the first structure, respectively; upper end surfaces of the lower front side plate and the lower rear side plate are provided to be a second structure having a second groove in the middle of the second structure, respectively; and when the upper shear box is placed opposite to the lower shear box, the first groove is placed opposite to the second groove, and the rock mass to be tested placed in the accommodating cavity is observed from outside.

10. The shear box for testing the cyclic shear characteristics of the rock mass discontinuity according to claim 3, wherein lower end surfaces of the upper front side plate and the upper rear side plate are provided to be a first structure having a first groove in the middle of the first structure, respectively; upper end surfaces of the lower front side plate and the lower rear side plate are provided to be a second structure having a second groove in the middle of the second structure, respectively; and when the upper shear box is placed opposite to the lower shear box, the first groove is placed opposite to the second groove, and the rock mass to be tested placed in the accommodating cavity is observed from outside.

11. The shear box for testing the cyclic shear characteristics of the rock mass discontinuity according to claim 4, wherein lower end surfaces of the upper front side plate and the upper rear side plate are provided to be a first structure having a first groove in the middle of the first structure, respectively; upper end surfaces of the lower front side plate and the lower rear side plate are provided to be a second structure having a second groove in the middle of the second structure, respectively; and when the upper shear box is placed opposite to the lower shear box, the first groove is placed opposite to the second groove, and the rock mass to be tested placed in the accommodating cavity is observed from outside.

12. The shear box for testing the cyclic shear characteristics of the rock mass discontinuity according to claim 5, wherein lower end surfaces of the upper front side plate and the upper rear side plate are provided to be a first structure having a first groove in the middle of the first structure, respectively; upper end surfaces of the lower front side plate and the lower rear side plate are provided to be a second structure having a second groove in the middle of the second structure, respectively; and when the upper shear box is placed opposite to the lower shear box, the first groove is placed opposite to the second groove, and the rock mass to be tested placed in the accommodating cavity is observed from outside.

13. The shear box for testing the cyclic shear characteristics of the rock mass discontinuity according to claim 6, wherein lower end surfaces of the upper front side plate and the upper rear side plate are provided to be a first structure having a first groove in the middle of the first structure, respectively; upper end surfaces of the lower front side plate and the lower rear side plate are provided to be a second structure having a second groove in the middle of the second structure, respectively; and when the upper shear box is placed opposite to the lower shear box, the first groove is placed opposite to the second groove, and the rock mass to be tested placed in the accommodating cavity is observed from outside.

14. The shear box for testing the cyclic shear characteristics of the rock mass discontinuity according to claim 7, wherein the lower end surfaces of the upper front side plate and the upper rear side plate are provided to be a first structure having a first groove in the middle of the first structure, respectively; the upper end surfaces of the lower front side plate and the lower rear side plate are provided to be a second structure having a second groove in the middle of the second structure, respectively; and when the upper shear box is placed opposite to the lower shear box, the first groove is placed opposite to the second groove, and the rock mass to be tested placed in the accommodating cavity is observed from outside.

* * * * *